United States Patent [19]

Negrych

[11] Patent Number: 4,820,545
[45] Date of Patent: Apr. 11, 1989

[54] METHOD OF BONDING CERAMIC ORTHODONTIC APPLIANCES

[75] Inventor: John A. Negrych, Westminster, Calif.

[73] Assignee: Ceradyne, Inc., Costa Mesa, Calif.

[21] Appl. No.: 912,286

[22] Filed: Sep. 29, 1986

[51] Int. Cl.$^4$ .......................... B44C 1/22; A01N 1/02; B05D 3/02; A61C 5/00

[52] U.S. Cl. ......................................... 427/2; 156/632; 427/190; 427/374.7; 427/376.2; 433/217.1; 433/228.1

[58] Field of Search ............... 427/2, 193, 190, 376.2, 427/374.4, 374.5, 374.6, 374.7; 106/35; 156/632; 433/8, 9, 217.1, 226, 228.1

[56] References Cited

U.S. PATENT DOCUMENTS

| | | | |
|---|---|---|---|
| 4,180,911 | 1/1980 | Bullock | 106/35 X |
| 4,215,033 | 7/1980 | Bowen | 106/35 X |
| 4,364,731 | 12/1982 | Norling et al. | 428/448 X |
| 4,435,160 | 3/1984 | Randklev | 106/35 X |
| 4,479,782 | 10/1984 | Orlowski et al. | 433/9 X |
| 4,486,179 | 12/1984 | Brauer et al. | 106/35 X |
| 4,595,598 | 6/1986 | De Luca et al. | 427/2 |

FOREIGN PATENT DOCUMENTS 0160481 11/1985 European Pat. Off. .

Primary Examiner—Michael Lusignan
Attorney, Agent, or Firm—Leonard Tachner

[57] ABSTRACT

A method of enhancing the bondability of ceramic orthodontic brackets or other dental attachments for improving the bonding strength between such attachments and the tooth engaging surface utilizing an intermediate bonding agent such as an acrylic resin. The method of the present invention results in the application of a silicious glass-like material coating of the bonding surface of the dental appliance. The silicious glass-like material provides three functions: (1) the proper surface chemistry for the use of organofunctional silanes that act as adhesion promoters or primers to enhance the bond between the adhesive and the orthodontic bracket; (2) a medium whereby second phase particulates can be adhered to the bracket to form irregular surface projections to enhance bonding; and (3) a surface that can be etched to yield macro and micro pitting to enhance the bond between the appliance and the intermediate bonding agent.

14 Claims, 1 Drawing Sheet

METHOD OF BONDING CERAMIC ORTHODONTIC APPLIANCES

BACKGROUND OF THE INVENTION

1. Field of the Invention

The present invention relates generally to the art of ceramic orthodontic appliances and more specifically, to methods for providing the ceramic material with a porous glassy coating of high mechanical strength to enhance the bonding of the ceramic material such as polycrystalline alumina and sapphire to the tooth enamel with an interlying acrylic resin material.

In orthodontic surgical procedures, orthodontic brackets are typically attached to teeth by adhesive bonding. The surface of the teeth is often acid etched so that a micro-mechanical interlock is achieved between the resin and the etched surface. Alternatively, the surface of the tooth may be provided with a crystal growth to which a resin material is bonded. There is also mechanical bond between the bracket base abutting the tooth and the resin. This mechanical bond normally represents the weak point of the assembly and brackets can become detached from the teeth by failure of the mechanical bond of the bracket resin interface if the shear strength thereof is exceeded. More recently, there has been a substantial interest developed in ceramic orthodontic appliances because of the inherent wear resistance of ceramic materials. In addition, certain ceramic materials show substantial promise for use in more cosmetic dental appliances wherein the dental brackets may be made far less obvious by using transparent or translucent ceramic materials therefor. In particular, it has been found that polycrystalline alumina and sapphire can be used to create extremely wear-resistant orthodontic bracket appliances which also have superior cosmetic appearance and which may therefore have a profound effect on the orthodontic industry by making the wearing of orthodontic appliances more amenable to the appearance concerns of adults and older teenagers. Unfortunately, the aforementioned bonding problem of prior art orthodontic materials is even more severe in regard to ceramic orthodontic appliances because such ceramic materials inherently have extremely hard surfaces which are more resistant to adherence to bonding materials.

2. Prior Art

Although there are numerous prior art references relating to the bonding of orthodontic appliances to the surface of teeth, the prior art with respect to the bonding of ceramic materials for this purpose is quite limited because of the relatively recent consideration of ceramic materials for orthodontic applications.

U.S. Pat. No. 3,895,445 to Silverman et al is directed to adhesive compositions for orthodontic applications and specifically includes a thermosetting resin composition which adheres to tooth enamel. The resin composition is etched using a methacrylic acid ester mixture to penetrate the thermosetting resin composition and allow increased adherence to the orthodontic appliances.

U.S. Pat. No. 3,955,282 to McNall is directed to a method of mounting orthodontic brackets to teeth. In this reference the tooth is etched by phosphoric acid and a pre-mixed dental adhesive attaches the orthodontic brackets to the teeth.

U.S. Pat. No. 4,180,911 to Bullock is directed to a method for direct bonding of orthodontic structures to teeth using a fluoride pre-treatment. The tooth is etched by acid and a solution of stannous fluoride is applied to the dried tooth surface to protect from the development of caries and also act as a bridging means between the tooth surface and the adhesive to enhance the bond strength.

U.S. Pat. No. 4,010,545 to Kilian et al is directed to adhesive bonding of orthodontic brackets to teeth. The tooth surface is acid etched, rinsed and dried. A thixotropic activated monomer is applied to the surface of the tooth or to the orthodontic bracket. The thixotropic activated monomer is activated prior to the application.

U.S. Pat. No. 3,625,916 to Newman is directed to a synthetic plastic dental adhesive. This reference is relevant because it relates to the use of silica and a filler selected from the group consisting of silica gel and pulverulent, fused quartz glass.

U.S. Pat. No. 4,068,379 to Miller et al discloses an orthodontic appliance with a porous tooth-abutting face. The appliance is bonded directly to a tooth utilizing a composite base with a porous tooth-abutting face. The base is formed by rolling a mesh in strip form to form flats on at least one surface of the mesh which is to be in contact with a solid base portion and then bonding the mesh to the base.

Canadian Patent No. 1,187,727 to Smith et al relates to the use of a particular coating applied to dental attachments on the tooth engaging surface thereof which coating enables improved bonding between the tooth and the dental attachment. Methods such as fusion or sintering may be used to apply the particular coating to the attachment. The coating may take the form of discrete particles spaced apart from each other on the surface of the form of a layer or multiple layers of particles bonded together to produce a network of interconnected pores.

Unfortunately, none of the prior art known to the applicant herein specifically addresses the problems associated with bonding an extremely hard ceramic material orthodontic bracket to the surface of a tooth. Accordingly, none of the prior art known to the applicant teaches or even suggests the particular solution of the present invention.

SUMMARY OF THE INVENTION

The present invention relates to a method of increasing the bondability of a ceramic material such as polycrystalline alumina or sapphire, to be bonded by means of an acrylic resin to the surface of tooth enamel. Basically, the method described herein produces a porous glassy coating which matches the coefficient of thermal expansion of the ceramic such as alumina or sapphire and engenders a wicking mechanism to enhance the bonding area of the acrylic resin. The siliceous glassy coating also provides a chemically compatible surface to allow the use of organofunctional silane adhesion promoters or primers, the use of which greatly enhances the bond strength of the appliance to the acrylic or other resin glue. Without the use of this primer the bond strength is too low to facilitate the successful use of the orthodontic appliance. As a result of the present invention the direct application of orthodontic and other dental attachments made from such ceramic materials is greatly facilitated.

Three alternative embodiments are disclosed herein. In one such embodiment a frit material such as powdered glass or glassy ceramic is applied to a polycrystalline or single crystal surface at the base of a ceramic dental bracket. The frit is then fired to a melt condition and cooled to a glass or glassy ceramic condition. It is then etched in hydrofluoric acid to increase the surface area as the silica content of the frit is removed at a higher rate than the ceramic content.

In a second embodiment the base of a dental bracket is coated with a glass or glassy ceramic with a frit containing between 10 and 30% by weight, 100 micron or larger particles of alumina. Such particles appear at the surface of the glass or glassy ceramic surface interface and greatly increase the surface area of the bond interface.

In still a third alternative embodiment of the present invention the alumina particles of the second embodiment of the invention are replaced by silica particles of the same size, namely, 100 microns or larger. After fritting, the large particles of silica are leached by immersion in hydrofluoric acid to produce a highly porous surface at the base of the dental bracket.

The organofunctional silane is applied to the etched surface by methods common to the bonding industry such as dipping, spraying or painting. After silanation the parts are dried and ready for bonding. It has been found that whereas unsilanated polycrystalline orthodontic brackets have a bond pull strength in the range of 2–6 pounds, silanated polycrystalline orthodontic brackets have a bond pull strength in the range of 38–62 pounds.

OBJECTS OF THE INVENTION

It is therefore a principal object of the present invention to provide a method for enhancing the bonding of ceramic material orthodontic appliances to the surface of teeth using acrylic resins or other glues.

It is an additional object of the present invention to provide a method for increasing the bondability of polycrystalline alumina and/or sapphire substrates in the form of orthodontic appliances whereby to permit exploitation of the structural and cosmetic advantagesous use of ceramic materials for orthodontic applications.

It is still an additional object of the present invention to provide a method for applying a glass or glassy ceramic material to the contact surface of a dental bracket and including a frit material such as powdered glass or powdered glassy ceramic which may be etched in a selected acid to increase the surface area of the contact portion of the ceramic bracket in order to improve the bonding between the bracket and the tooth.

It is still an additional object of the present invention to provide the increased surface area of a ceramic dental bracket as described in the above disclosed object of the invention, but by utilizing a frit containing a preselected quantity by weight of a minimum size of particles of either alumina or silica for increasing the surface area of the dental bracket contact portion.

It is still an additional object of the present invention to provide a siliceous surface to which an organofunctional silane adhesion promoter or primer bonds and enhances the adhesion between the orthodontic appliance and the acrylic resin or other glues.

BRIEF DESCRIPTION OF THE DRAWINGS

The aforementioned objects and advantages of the present invention as well as additional objects and advantages thereof will be more fully understood hereinafter as a result of a detailed description of preferred embodiments of the invention when taken in conjunction with the accompanying drawing which represents an orthodontic appliance treated in accordance with the methods of the present invention and indicating its relative position after being bonded to the enamel surface of a tooth.

DETAILED DESCRIPTION OF PREFERRED EMBODIMENTS

Figure 1:
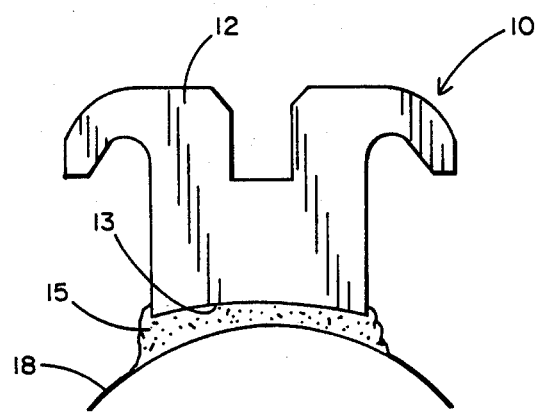

The method of the present invention may be best understood by first referring to FIG. 1 wherein a dental bracket or comparable orthodontic appliance 10 is illustrated and comprises a ceramic appliance body 12 having a bonding surface 13 which is adapted by means of the present invention to be bonded to a tooth 18 by an intermediate bonding agent 15 such as an acrylic resin. Normally the bonding of a hard ceramic surface such as sapphire or crystalline alumina directly to an acrylic resin produces a weak joint at best. However, increasing the surface area of the bonding region on the ceramic orthodontic appliance increases the pull strength of the bond. The method of the present invention is used to significantly increase the strength of the bond between the bracket 12 and the acrylic resin 15 along the surface 13 by applying a coating of glass (silica) which substantially matches the coefficient of expansion of the ceramic material but more importantly by significantly increasing the surface area of the glass coating along surface 13 to overcome the otherwise inherently weak joint between the ceramic and the acrylic.

Three alternative embodiments of the method of the present invention are disclosed herein to increase the bondability of the ceramic bracket to the acrylic resin and thus to the tooth. As a result, the direct application of orthodontic and other dental attachments made from selected ceramic materials is greatly facilitated. The first embodiment of the present invention comprises the steps of applying the glass or glassy ceramic material, (generically referred to herein as glass-like material), which has a high silica content and which in fact comprises a frit material incluidng powdered glass or powdered glassy ceramic. This frit material is applied to the surface 13 of the bracket 12 which may be way of example comprise polycrystalline alumina or sapphire, both of which have proved to be cosmetically appealing as well as significantly wear resistant for use in orthodontic appliances. After the frit material is applied to the surface 13 the frit is fired, that is, heated to a melt temperature and then allowed to cool. The surface 13 having the frit coating thereon is then etched in an appropriate acid such as hydrofluoric acid. The silica content of the glass-like material coating on the surface 13 will be removed in the acid at a higher rate than the ceramic content of the frit and as a result the coating applied to surface 13 will become pitted depending upon the length of time of the etching. The pitting of course increases the total surface area of the surface 13 and the combined wicking action of the porous glassy coating as well as the increased surface area caused by the etching action of the hydrofluoric acid on the silica content of the coating, significantly enhance the strength of the bond between the bracket 12 and the acrylic 15 along the surface 13. The bonding is further enhanced and facilitated by applying an organofunctional silane adhesion promoter to the etched high surface area of the siliceous frit coating. Standard techniques as designated by manufacturers of these materials such as Dow Corning or Union Carbide can be used to paint, dip or spray the silane coupling agents onto the surface.

In an alternative embodiment of the present invention the glass-like material frit contains between 10 and 30% by weight particles of alumina which are preferably at least 100 microns in size. Such particles appear at the surface of the glass-like ceramic surface interface and thereby greatly increase the surface area of the bond interface along surface 13.

In yet another embodiment of the present invention instead of using alumina particles to enhance the bonding surface area, one utilizes silica particles that are also at least 100 microns in size. After the frit coating is applied to the tooth the large silica particles are then immersed in an etching acid such as hydrofluoric to produce a highly porous surface at the base of the dental bracket 12. The second embodiment produces an increased surface area by, in effect, creating a glassy coating along the surface 13 that has a plurality of relatively large irregular projections. On the other hand, the third embodiment results in an increased surface area wherein the applied glassy coating has a plurality of irregularly surfaced depressions or dimples resulting from the removal of the silica by the etching acid.

Those having skill in the art to which the present invention pertains will now as a result of the teaching herein understand that the present invention pertains to a method for increasing the bond strength between a ceramic and acrylic resin and more specifically to a method for increasing the bond strength between a ceramic orthodontic appliance and the surface of a tooth where, for example, an acrylic resin is employed as a bonding agent. Three alternative embodiments have been disclosed herein each directed toward achieving a substantially identical result, namely, the application of glassy coating to the bonding surface of the ceramic dental appliance having a significantly enhanced surface area due to the etching of silica particles or the retention of alumina particles as projections of the bonding surface. It will be further understood that various modifications and additions may be made to the present invention. By way of example, although specific ceramic materials, coating materials and surface area generating materials have been disclosed herein, it will be understood that various alternative materials may also be employed without departing from the teaching of the invention. Accordingly, the scope of the present invention is to be limited only by the claims appended hereto.

I claim:

1. A method for increasing the bond strength between a ceramic and a bonding agent such as acrylic resin, the method comprising the steps of:
   applying a glass-like material coating to the ceramic, said glass-like material coating having particles of powdered glass-like material therein and having a pre-selected content of silica in said particles;
   firing said glass-like material coating to a temperature sufficient to melt said particles;
   cooling said glass-like material coating to harden same; and
   etching said glass-like material coating to remove said silica whereby to increase the surface area of said coating for increasing the area for receiving said acrylic resin; and
   silanating said etched glass-like material coating with an organofunctional silane adhesion promoter.

2. The method recited in claim 1 wherein said ceramic is taken from the group consisting of polycrystalline alumina and sapphire.

3. The method recited in claim 2 wherein said ceramic is in a single crystalline form.

4. The method recited in claim 2 wherein said ceramic is in a polycrystalline form.

5. The method recited in claim 1 wherein said particles comprise entirely silica and are at least 100 microns in size.

6. The method recited in claim 1 wherein said ceramic is formed into the shape of an orthodontic appliance and said bonding agent is used as a bonding interface between said appliance and the surface of a tooth.

7. The method recited in claim 1 wherein said glass-like material is taken from the group consisting of glass and glassy ceramics.

8. The method recited in claim 1 wherein said acid is hydrofluoric acid.

9. A method for increasing the bond strength between a ceramic orthodontic appliance and the surface of a tooth where an acrylic resin is employed as the bonding agent; the method comprising the step of coating the bonding surface of said appliance with a glass-like frit containing between 10 and 30% by weight particles of alumina of at least 100 microns for increasing the surface area of said bonding surface.

10. The method recited in claim 9 wherein said ceramic is taken from the group consisting of alumina and sapphire.

11. A method for increasing the bond strength between a ceramic and a bonding agent such as acrylic resin, the method comprising the steps of:
    melting a glass-like material coating on the ceramic and allowing said coating to cool until it is in a hardened state; and
    silanating said coating with an organofunctional silane adhesion promoter.

12. The method recited in claim 11 wherein said ceramic is polycrystalline alumina.

13. A method for increasing the bond strength between a ceramic and a bonding agent such as acrylic resin; the method comprising the steps of:
    applying a glass-lke material coating to the ceramic;
    firing said glass-like material coating until it melts;
    cooling said glass-like material coating to harden same; and
    silanating said glass-like material coating with an organofunctional silane adhesion promoter.

14. The method recited in claim 13 wherein said ceramic is polycrystalline alumina.

* * * * *

UNITED STATES PATENT AND TRADEMARK OFFICE
CERTIFICATE OF CORRECTION

PATENT NO. : 4,820,545
DATED : April 11, 1989
INVENTOR(S) : John A. Negrych

It is certified that error appears in the above—identified patent and that said Letters Patent is hereby corrected as shown below:

Title page, change Appl. No.: 912,286 to --Appl. No.: 912,288--.

Signed and Sealed this

Seventh Day of May, 1991

Attest:

HARRY F. MANBECK, JR.

*Attesting Officer*  *Commissioner of Patents and Trademarks*